(12) United States Patent
Kanda et al.

(10) Patent No.: US 6,527,745 B1
(45) Date of Patent: Mar. 4, 2003

(54) IRRIGATION-ASPIRATION APPARATUS

(75) Inventors: Hidenori Kanda, Aichi (JP); Hiroyuki Tashiro, Aichi (JP); Hisatoshi Kato, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/679,309

(22) Filed: Oct. 6, 2000

(30) Foreign Application Priority Data

Oct. 6, 1999 (JP) .......................................... 11-285309
Sep. 8, 2000 (JP) ...................................... 2000-278688

(51) Int. Cl.⁷ .............................................. A61M 1/00
(52) U.S. Cl. .......................... 604/151; 604/19; 604/27; 604/35
(58) Field of Search ............................. 604/19, 22, 27, 604/30, 31, 35, 65, 118–120, 151, 153; 128/DIG. 12, DIG. 13; 417/477.3

(56) References Cited

U.S. PATENT DOCUMENTS 5,098,387 A * 3/1992 Wiest et al. ................. 417/475
5,195,960 A * 3/1993 Hossain et al. ...... 128/DIG. 12
5,499,969 A * 3/1996 Beuchat et al. ...... 128/DIG. 12
5,526,844 A * 6/1996 Kamen et al. ......... 137/565.16
5,538,405 A 7/1996 Patno et al. ................. 417/326

FOREIGN PATENT DOCUMENTS

JP  9-502783  3/1997  ........... F04B/43/12
JP  10-155830  6/1998  ........... A61F/9/007

* cited by examiner

Primary Examiner—Timothy L. Maust
(74) Attorney, Agent, or Firm—Sughrue Mion, PLLC (57) ABSTRACT

In a peristaltic aspiration pump, a plurality of rollers are equally spaced apart from a rotating shaft and rotatable about the rotating shaft. The rollers sequentially compress and occlude an aspiration tube to generate a vacuum pressure within the aspiration tube. An irrigation-aspiration apparatus aspirates tissue to be removed together with an irrigation fluid supplied to an operated part via the aspiration tube, using the peristaltic aspiration pump. The peristaltic aspiration pump is driven under control to change the travelling speed of the roller in accordance with statuses of occluding the aspiration tube.

15 Claims, 6 Drawing Sheets

IRRIGATION-ASPIRATION APPARATUS

BACKGROUND OF THE INVENTION

The present invention relates to an irrigation-aspiration apparatus that supplies an irrigation fluid into an operated part (an affected part) and which aspirates the supplied irrigation fluid together with tissue to be removed from the affected part, and more particularly to a mechanism suitable for attenuating the pulsation (ripple) arising owing to a peristaltic aspiration pump (suction pump).

An irrigation-aspiration apparatus is known that supplies an irrigation fluid into an affected part and which aspirates the supplied irrigation fluid together with tissue to be removed from the affected part. For example, it is used in cataract surgery or vitreous surgery in the ophthalmic field.

In the irrigation-aspiration apparatus for use in these surgeries, a hand-piece is used to aspirate the supplied irrigation fluid together with the tissue to be removed from the affected part within the eyeball. The removed tissue is drawn in through an aspiration hole at the distal end of the hand-piece tip together with the supplied irrigation fluid by using a vacuum pressure (an aspiration pressure) generated by an aspiration pump (a suction pump) and thereafter drained through an aspiration tube connecting to the hand-piece into the inside of a drainage bag. A peristaltic aspiration pump is typically used as the aspiration pump which aspirates the tissue to be removed.

Figure 6A:
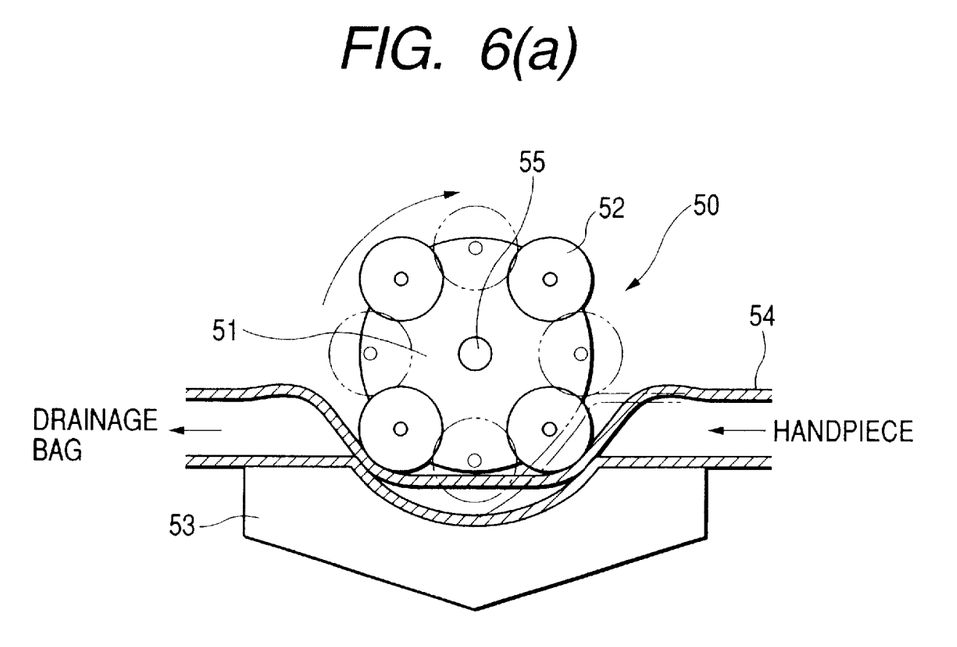
FIG. 6 is a schematic view of the essence of a typical peristaltic aspiration pump.

In the peristaltic aspiration pump, as shown in FIG. 6(a), a plurality of pump rollers 52 are disposed on the same circumference (spaced apart at equal distance around a rotating shaft 55) on a rotating plate (a rotating support) 51. When the rotating plate 51 revolves, the rollers 52 compress and occlude an aspiration tube 54 placed between an aspiration pump 50 and a tube receptacle (tube retainer) 53 as the pump rollers 52 rotate. The fluid in the aspiration tube 54 is pushed forward in the direction in which the pump rollers 52 rotate, thereby producing a vacuum pressure.

Figure 6B:
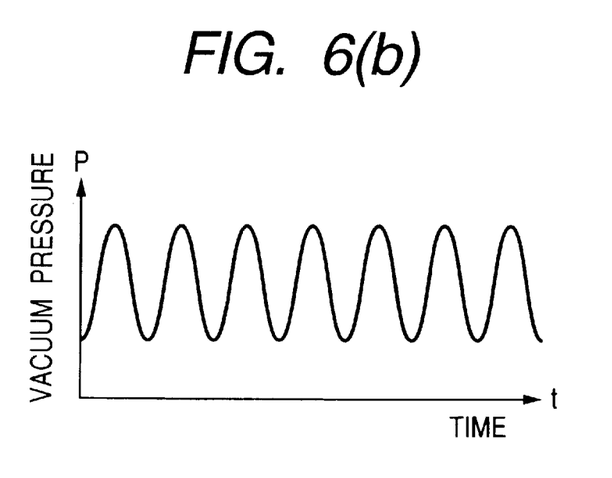

The peristaltic aspiration pump constructed as described above, however, encounters the following problem: During a first status lasting from a condition in which one of the pump rollers 52 starts compressing and occluding the aspiration tube 54 to a condition in which the one pump roller 52 completely occludes the aspiration tube 54, the area of flow passage within the aspiration tube 54 is reduced, and consequently the quantity of aspiration flow and thus the flow rate of aspiration flow is decreased. Thereafter, during a second status lasting from the condition in which the one pump roller 52 completely occludes the aspiration tube 54 to the condition in which another subsequent one of the pump rollers 52 starts compressing and occluding the aspirating tube 54, the aspiration tube 54 is released from the one pump roller 52 and restored by own resilience to increase the area of flow passage within the aspiration tube 54. Consequently, the flow rate in the direction in which the pump rollers revolve is increased, and the quantity of aspiration flow is increased. Since the decrease and increase in quantity of aspiration flow associated with the first and second statuses are repeated, there occur periodic sinusoidal fluctuations in vacuum pressure or quantity of aspiration flow, which is called pulsation, as shown in FIG. 6B. This pulsation may cause pressure variations in the eye under operation, occasionally making it difficult to achieve correct control in the vacuum pressure and the quantity of aspiration flow.

SUMMARY OF THE INVENTION

The present invention has been accomplished in the light of the above-mentioned problem, and has, as an object, providing an irrigation-aspiration apparatus which is capable of suppressing the pulsation caused by a peristaltic aspiration pump to thereby secure a stable vacuum pressure and stable quantity of aspiration flow.

In order to solve the above-mentioned problems, the present invention provides the following configuration.

1. An irrigation-aspiration apparatus for supplying an irrigation fluid to a subject part under operation and aspirating the supplied irrigation fluid and tissue removed from the subject part, the apparatus comprising:
    an aspiration tube through which the supplied fluid and the removed tissue is aspirated and disposed of;
    a peristaltic aspiration pump having a plurality of rotatable rollers that travel to compress and occlude the aspiration tube to thereby generate a vacuum pressure in the aspiration tube; and
    control means for driving and controlling the peristaltic aspiration pump to vary a travelling speed of the roller in accordance with statuses of occluding the aspiration tube.

2. The apparatus of 1, wherein the control means drives and controls the peristaltic aspiration pump so that the travelling speed is increased during a first status lasting from a condition in which one of the rollers first starts occluding the aspiration tube and to a condition in which the one roller occludes the aspiration tube substantially completely, and the travelling speed is decreased during a second status lasting from the condition in which the one roller occludes the aspiration tube substantially completely to a condition in which a subsequent one of the rollers starts occluding the aspiration tube.

3. The apparatus of 2, wherein the control means drives and controls the peristaltic aspiration pump so that the travelling speed presents a substantially square wave form.

4. The apparatus of 2, wherein the control means drives and controls the peristaltic aspiration pump so that the travelling speed presents a substantially sinusoidal form.

5. The apparatus of 1, wherein the rollers are arranged equidistantly from a rotational axis, and rotatingly travel about the rotational axis.

6. An irrigation-aspiration apparatus for supplying an irrigation fluid to a subject part under operation and aspirating the supplied irrigation fluid and tissue removed from the subject part, the apparatus comprising:
    an aspiration tube through which the supplied irrigation fluid and the removed tissue is aspirated and disposed of;
    a peristaltic aspiration pump having a plurality of rotatable rollers that travel to compress and occlude the aspiration tube to thereby generate a vacuum pressure in the aspiration tube; and
    control means for driving and controlling the peristaltic aspiration pump to vary a travelling speed of the roller in accordance with a travelling rotation angle of the roller.

7. The apparatus of 6, wherein the control means drives and controls the peristaltic aspiration pump so that the travelling speed is increased once and decreased once when one of the rollers travels by a predetermined amount of the travelling rotation angle.

8. The apparatus of 7, wherein the predetermined amount of the travelling rotation angle is determined depending on the number of the rollers provided in the peristaltic aspiration pump.

9. The apparatus of 7, wherein the control means drives and controls the peristaltic aspiration pump so that the travelling speed presents a substantially square wave form.

10. The apparatus of 7, wherein the control means drives and controls the peristaltic aspiration pump so that the travelling speed presents a substantially sinusoidal form.

11. The apparatus of 6, wherein the rollers are arranged equidistantly from a rotational axis, and rotatingly travel about the rotational axis.

12. An irrigation-aspiration apparatus for supplying an irrigation fluid to a subject part under operation and aspirating the supplied irrigation fluid and tissue removed from the subject part, the apparatus comprising:

an aspiration tube through which the supplied irrigation fluid and the removed tissue is aspirated and disposed of;

a peristaltic aspiration pump having a plurality of rotatable rollers that travel to compress and occlude the aspiration tube to thereby generate a vacuum pressure in the aspiration tube; and control means for driving and controlling the peristaltic aspiration pump to vary a travelling speed of the roller in conformity with variations in vacuum pressure or quantity of aspiration flow.

13. The apparatus of 12, wherein the control means drives and controls the peristaltic aspiration pump so that, if the vacuum pressure or the quantity of the aspiration flow is varied to be smaller, the travelling speed is larger, and if the vacuum pressure or the quantity of the aspiration flow is varied to be larger, the travelling speed is smaller.

14. The apparatus of 13, wherein the control means drives and controls the peristaltic aspiration pump so that, if the vacuum pressure or the quantity of the aspiration flow is minimal, the travelling speed is the largest, and if the vacuum pressure or the quantity of the aspiration flow is maximum, the travelling speed is the smallest.

15. The apparatus of 13, wherein the control means drives and controls the peristaltic aspiration pump so that the travelling speed presents a substantially square wave form.

16. The apparatus of 13, wherein the control means drives and controls the peristaltic aspiration pump so that the travelling speed presents a substantially sinusoidal form.

17. The apparatus of 12, wherein the rollers are arranged equidistantly from a rotational axis, and rotatingly travel about the rotational axis.

The present disclosure relates to the subject matter contained in Japanese patent application Nos. Hei. 11-285309 (filed on Oct. 6, 1999), and 2000-278688 (filed on Sep. 8, 2000), which are expressly incorporated herein by reference in their entirety.

DESCRIPTION OF THE PREFERRED EMBODIMENT

Figure 1:
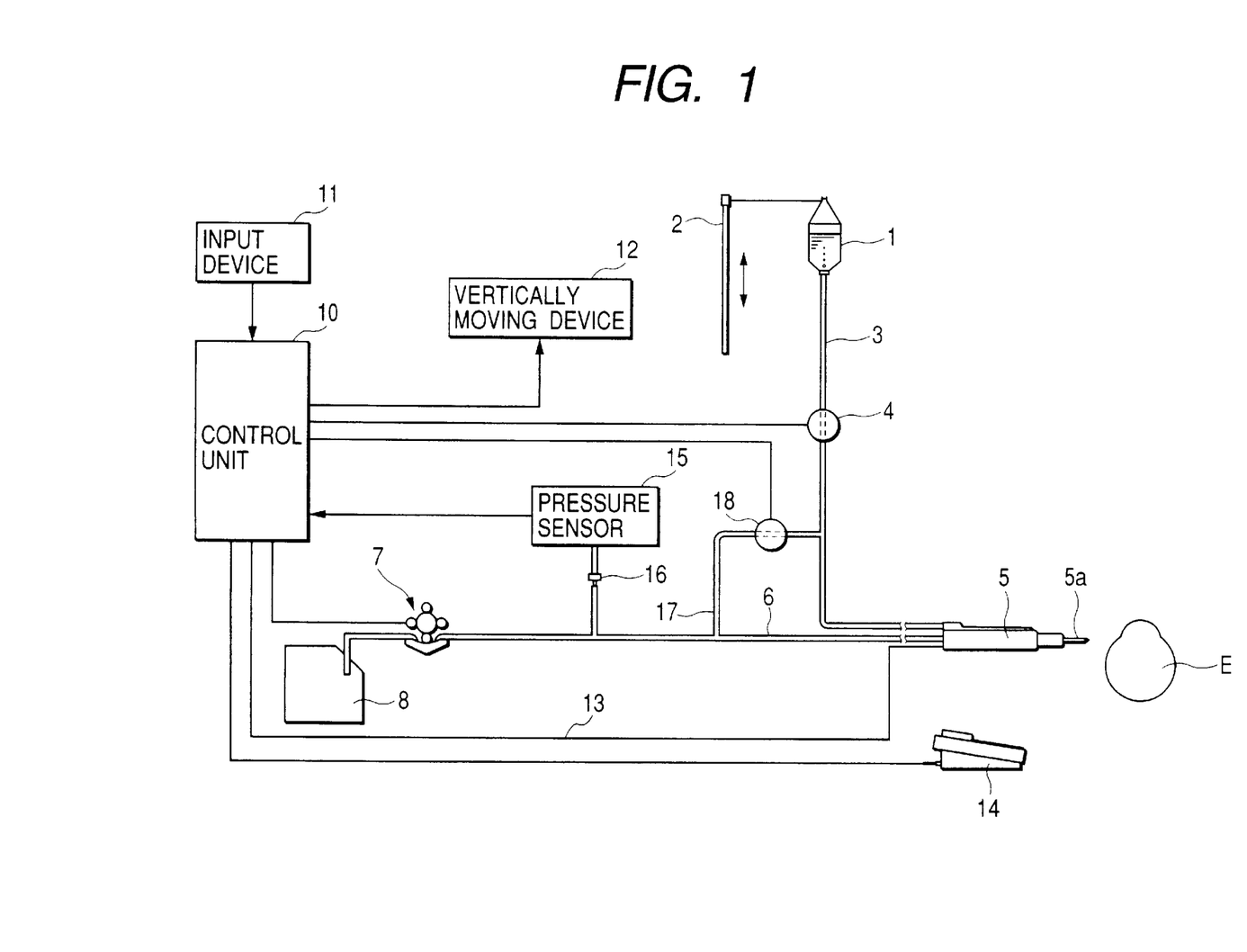
FIG. 1 is a schematic view of the essence of an irrigation-aspiration apparatus according to an embodiment of the present invention.

An irrigation-aspiration apparatus for use in cataract surgery according to one embodiment of the present invention will be described below with reference to accompanying drawings. FIG. 1 is a schematic view showing the arrangement of an irrigation-aspiration apparatus of the embodiment.

An irrigating bottle 1 filled with an irrigation fluid is hung on an irrigation pole 2. The irrigation pole 2 is vertically moved by a vertically moving device 12 in accordance with the height that is set for the pole 2 by an input device 11. The height of the bottle 10 is changed by the up/down movement of the irrigation pole 2 so as to adjust an irrigation pressure.

The irrigation fluid from the irrigation bottle 1 passes through an irrigation tube 3 to be supplied to the patient's eye E via an operation handpiece 5 held by a surgeon. A control valve 4 is provided midway of the irrigation tube 3, and opened or closed to control the outflow of the irrigation fluid. In this embodiment, as the operation handpiece 5, a US handpiece is used, which emulsifies and aspirates an opaque and hardened nucleus of a lens due to cataract using ultrasonic vibrations of a cutting tip 5a provided at the distal end. Ultrasonic vibrations of the cutting tip 5a are generated by applying electric power to a ultrasonic vibrator within the handpiece 5 via a power cable 13.

The handpiece 5 is connected to one end of a flexible irrigation tube 6. Provided midway of the rearward section of the aspiration tube 6 are a connecting section 16 connecting to a pressure sensor 15, and a peristaltic aspiration pump (suction pump) 7. Also, the aspiration tube 6 is in communication via a bypass tube 17 to the irrigation tube 3. The control valve 18 controls the flow out of the bypass tube 17. The pressure sensor 15 normally detects a vacuum pressure (an aspirating pressure) When the vacuum pressure rises above a preset value, the control valve 18 is opened under the control of a control unit 10, as required, so that the irrigation fluid is passed from the irrigation tube 3 via the bypass tube 17 into the aspiration tube 6, thereby decreasing the vacuum pressure. The upper limit of vacuum pressure is set by switch operation of the input device 11.

The irrigation fluid and the removed tissue are sucked through an aspiration hole provided at the distal end of the cutting tip 5a of the handpiece 5, and drained via the aspiration tube 6 and the aspiration pump 7 into a drainage bag 8. The control unit 10 controls the drive of the aspiration pump 7 to adjust the vacuum pressure, based on a signal depending on foot position of a foot switch 14 or a preset value input from the input device 11.

Figure 2:
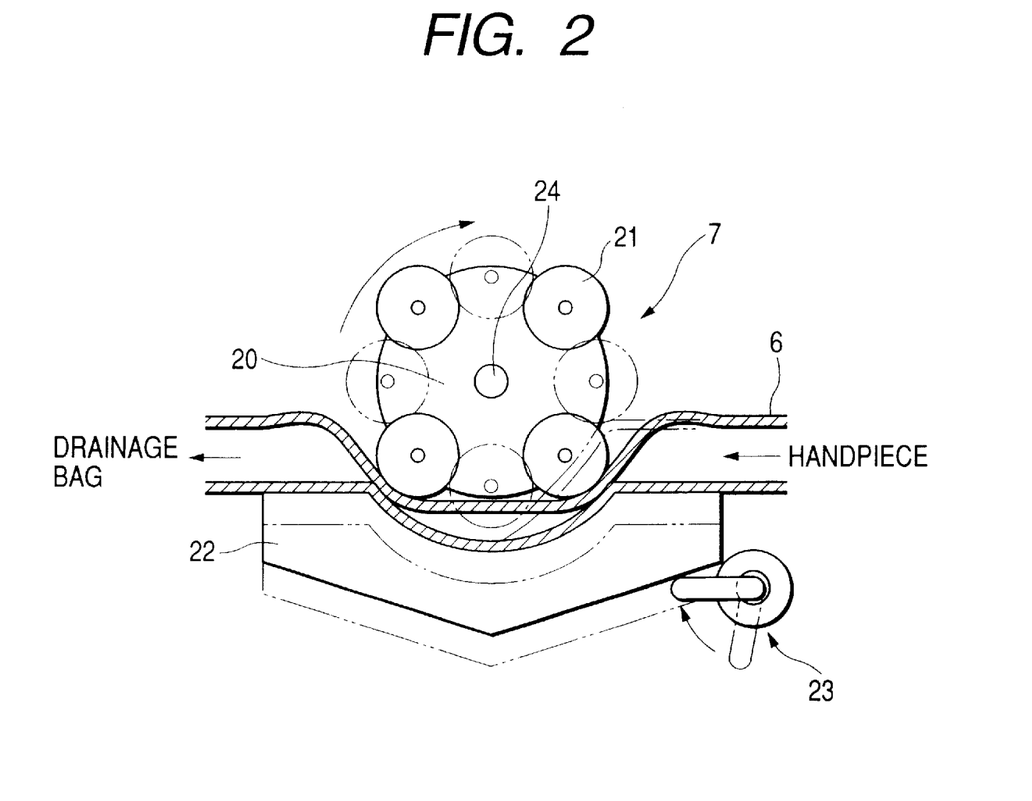
FIG. 2 is a schematic view of the essence of a peristaltic aspiration pump.

The aspiration pump 7 comprises a rotating plate (a rotating support) 20, four pump rollers 21 which are disposed rotatably on the circumference of the rotating plate 20 (spaced apart at equal distance with respect to the rotating shaft 24), and a tube receptacle (a tube retainer) 22, as shown in a schematic view of the essence of the peristaltic aspiration pump of FIG. 2. The tube receptacle 22 is vertically movable by the operation of a lever 23, so that the aspiration tube 6 can be readily placed between the aspiration pump 7 and the tube receptacle 22. When the rotating plate 20 revolves, the four pump rollers 21 travel to sequentially compressing and occluding the aspiration tube 6 while rotating. This operation causes the movement of the fluid in the aspiration tube 6, thereby imparting the vacuum pressure.

Figure 3A:
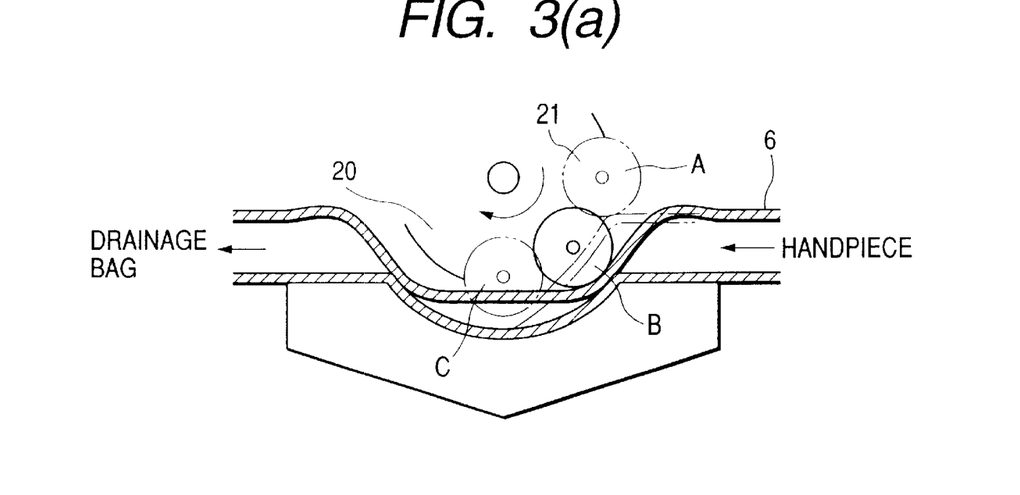
FIG. 3 is an explanatory view of the drive control of the aspiration pump.
Figure 3B:
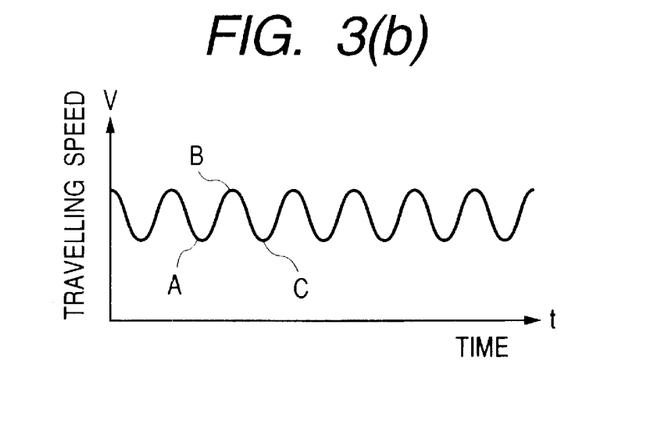
Figure 3C:
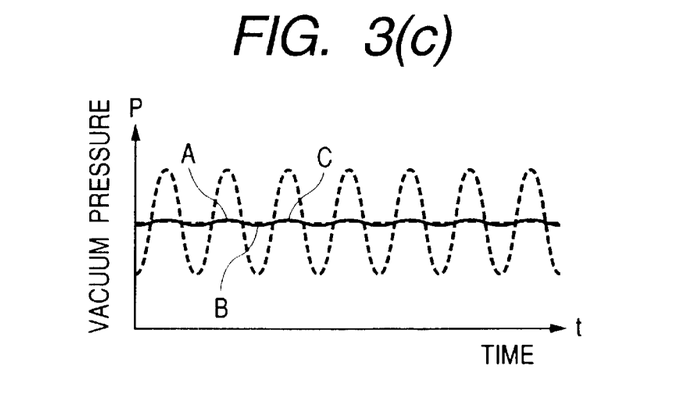

The drive control for the aspiration pump 7 to attenuate the pulsation in the irrigation-aspiration apparatus having the above-described configuration will be described with reference to an explanatory view of the drive control for the aspiration pump 7 as shown in FIG. 3. FIG. 3A is a view for explaining drive positions of the pump roller 21 when the pump roller 21 compresses and occludes the aspiration tube 6. FIG. 3B is a view showing the periodical changes in the travelling speed (or rotation speed of the rotating plate) V at which the pump roller 21 rotates. FIG. 3C is a view showing the periodical changes in the vacuum pressure P. The changes in vacuum pressure of the peristaltic aspiration pump which rotates at steady (constant) rate are indicated by the dot-line in FIG. 3C.

As shown in FIG. 3A, during a first status lasting from a position A where a pump roller 21 starts compressing and occluding the aspiration tube 6 to a position B where the pump roller 21 first completely occludes (completely closes) the aspiration tube 6, the flow passage of the aspiration tube 6 in the handpiece 5 side is gradually narrowed. Accordingly, during the first status in which the pump roller 21 travels in this section between the positions A and B, the quantity of aspiration flow decreases gradually. When the pump roller 21 reaches the position B, the quantity of aspiration flow is minimal and the vacuum pressure is the lowest.

On the other hand, during a second status lasting from the position B where the pump roller 21 first completely occludes the aspiration tube 6 to a position C where a subsequent pump roller 21 starts compressing and occluding the aspiration tube 6 to(the subsequent pump roller 21 reaches the position A), the aspiration tube 6 is released from the pressure of the pump roller 21 and restored due to own resiliency, and the flow passage of the aspiration tube 6 in the handpiece 5 side is gradually made larger. Accordingly, during the second status in which the pump roller 21 travels in this section between the positions B and C, the quantity of aspiration flow increases gradually. When the pump roller 21 reaches the position C, the quantity of aspiration flow is maximum and the vacuum pressure is the greatest. The above operation is repeated so that a vacuum pressure is produced continuously within the aspiration tube 6.

Considering the variations in vacuum pressure caused by the positional relation of the pump roller 21, as described above, the control unit 10 controls the travelling speed of the pump roller 21 (i.e. the rotational speed of the rotating plate 20) V to vary as shown in FIG. 3B. That is, during the first status in which the pump roller 21 rotatingly travels in the section A-B, since the quantity of aspiration flow decreases gradually as described above, the control unit 10 gradually increases the travelling speed of the pump roller 21 to reach the maximum travelling speed at the position B. In the section A-B, since compressing and occluding the aspiration tube 6 will cause the gradual reduction in the vacuum pressure, the control unit 10 increases the travelling speed of the pump roller 21 to suppress the reduction in the vacuum pressure.

On the other hand, during the second status in which the pump roller 21 rotatingly travels in the section B-C, since the quantity of aspiration flow increases gradually, the control unit 10 gradually decreases the travelling speed of the pump roller 21 to reach a minimum travelling speed at the position C. In the section B-C, since the aspiration tube 6 is restored gradually and therefore the quantity of aspiration flow is made large to increase the vacuum pressure, the travelling speed of the pump roller 21 is reduced, thereby suppressing abrupt rise in the vacuum pressure.

As described above, the travelling speed of the pump roller 21 is controlled to present a substantially sinusoidal form in accordance with the statues where the pump roller 21 compresses and occludes the aspiration tube 6, that is, in accordance with fluctuations of a sinusoidal form in the vacuum pressure (the quantity of aspiration flow) associated with the rotating travel of the pump rollers 21. By this control, the fluctuations in vacuum pressure can be suppressed, as indicated by the solid line of FIG. 3C, and thus the changes in pressure within the eye under surgery can be reduced.

The travelling speed of the pump roller 21 may be controlled to present a substantially square wave (pulse wave) form in accordance with the statues where the pump roller 21 compresses and occludes the aspiration tube 6, that is, in accordance with fluctuations in the vacuum pressure (the quantity of aspiration flow) associated with the rotating travel of the pump rollers 21. This control can also suppress the fluctuations in vacuum pressure.

Figure 4A:
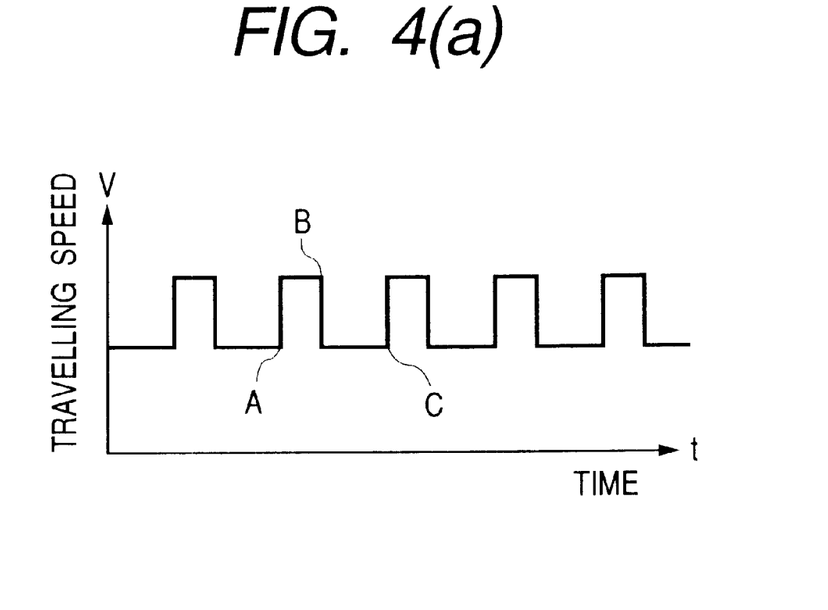
FIG. 4 is an explanatory view of a modification of the drive control of the aspiration pump.

Under the control by the control unit 10, the travelling speed of the pump rollers 21 (the rotation speed of the rotating plate 20) V is changed as shown in FIG. 4A. That is, during the first status in which the pump roller 21 rotatingly travels in the section A-B, since the quantity of aspiration flow gradually decreases, the control unit 10 increases (or speeds up) the travelling speed of the pump roller 21 to a speed higher by a certain amount than a predetermined reference speed. Conversely, during the second status in which the pump roller 21 travels in the section B-C, since the quantity of aspiration flow gradually increases, the control unit 10 reduces (or speeds down) the travelling speed of the pump roller 21 to be the predetermined reference speed. This control can suppress the fluctuations in vacuum pressure, and the changes in pressure within the eye under surgery.

Figure 4B:
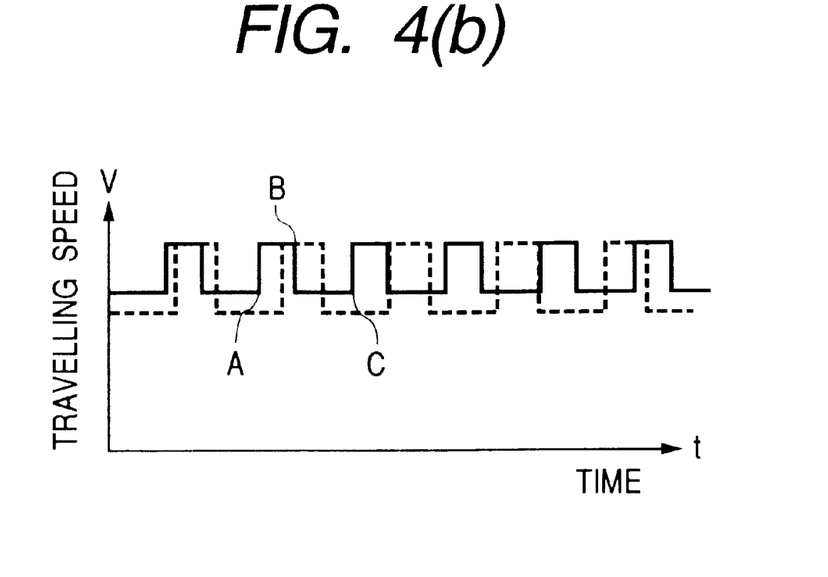

If such a quantity of aspiration flow is obtained as to be greater than an average quantity of aspiration flow obtained by an average travelling speed of the pump roller 21, the reference speed alone may be increased as shown in FIG. 4B, or the reference speed and the increased travelling speed may be both increased.

The travelling speed of the pump roller 21 can be changed in accordance with the positions of the travel or the angles of rotation in conformity with statuses of occluding the aspiration tube, i.e. fluctuations in vacuum pressure (quantity of aspiration flow). For example, in the case where a pulse motor with a full step of 1.8° is used to rotate the shaft 24 secured to the rotating plate 20, the travelling speed of the pump roller 21 can be readily controlled in accordance with the angle of rotation, because the pulse motor is rotated 0.45° per pulse.

For example, in the case where four pump rollers 21 are arranged, it suffices that the travelling speed of the pump roller 21 is increased or decreased repetitively, every time the pump roller 21 rotates about 45° (including about ±5°). In other words, the travelling speed is increased once and decreased once as one cycle during the travelling rotation angle of 90° (360°/4: number of pump rollers) of the pump roller 21 (if the pump roller 21 travels at the increased travelling speed during the travelling rotation angle of 42°, the pump roller 21 travels at the decreased travelling speed during the travelling rotation angle of 48°). Similarly, in the case where six pump rollers 21 are arranged, it suffices that the travelling speed of the pump roller 21 is increased or decreased repetitively, every time the pump roller 21 rotates about 30° (including about ±5°). In other words, the travelling speed is increased once and decreased once as one cycle during the travelling rotation angle of 60° (360°/6: number of pump rollers) of the pump roller 21 (if the pump roller 21 travels at the increased travelling speed during the travelling rotation angle of 27°, the pump roller 21 travels at the decreased travelling speed during the travelling rotation angle of 33°) In this way, the control unit 10 can control and change the travelling speed in accordance with the travelling rotation angle easily regardless of the number of pump rollers 21.

Figure 5:
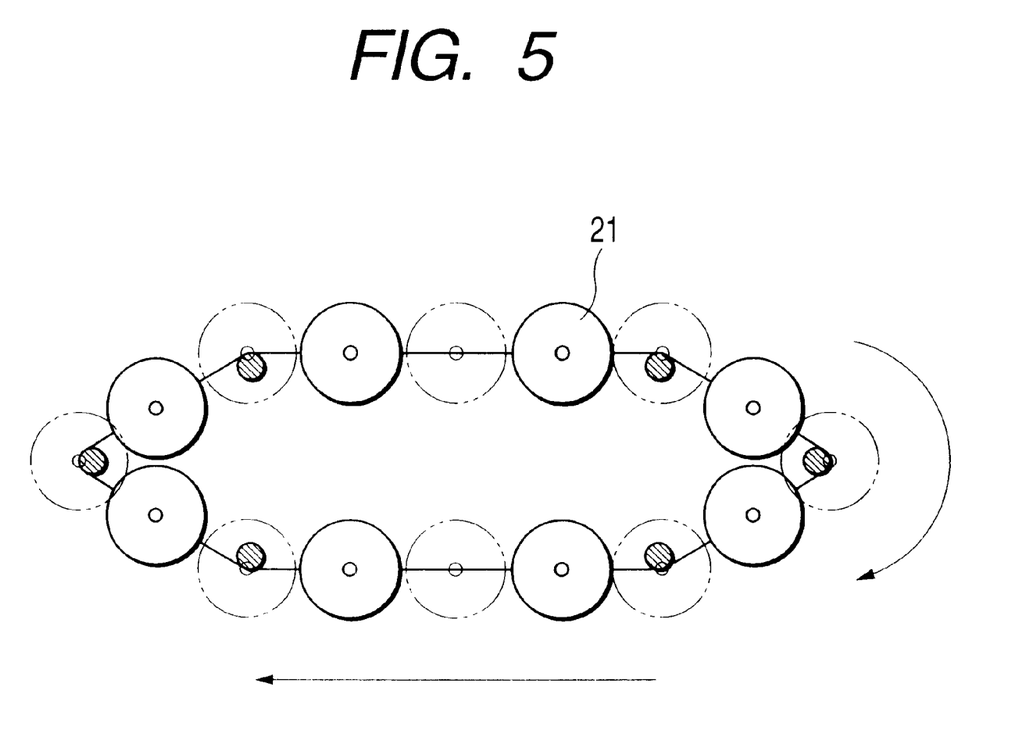
FIG. 5 is an explanatory view of a modification of the arrangement of the pump rollers.

In this embodiment, the pump rollers 21 travels to rotate about the rotating shaft 24. However, the travelling of the pump rollers 21 may include linear motion as shown in FIG. 5. Of course, the number of pump rollers is not be limited to four.

As described above, the pulsation produced by a peristaltic aspiration pump can be suppressed, and the fluctuations in pressure within the eye under surgery can be reduced. Also, stable vacuum pressure and stable quantity of aspiration flow can be obtained.

What is claimed is:

1. An irrigation-aspiration apparatus for supplying an irrigation fluid to a subject part under operation and aspirating the supplied irrigation fluid and tissue removed from the subject part, the apparatus comprising:

an aspiration tube through which the supplied fluid and the removed tissue is aspirated and disposed of;

a peristaltic aspiration pump having a rotating support provided with a plurality of rollers that rotatingly travel about a rotational axis of the rotating support to compress and occlude the aspiration tube to thereby generate a vacuum pressure in the aspiration tube; and control means for controlling rotation of the rotating support so that a rotational speed of the rotating support is increased and decreased at predetermined intervals during one rotation of the rotating support.

2. The apparatus of claim 1, wherein the control means controls the rotation of the rotating support so that the rotational speed is increased during a first status lasting from a condition in which one of the rollers first starts occluding the aspiration tube to a condition in which the one roller occludes the aspiration tube substantially completely, and the rotational speed is decreased during a second status lasting from the condition in which the one roller occludes the aspiration tube substantially completely to a condition in which a subsequent one of the rollers starts occluding the aspiration tube.

3. The apparatus of claim 2, wherein the control means controls the rotation of the rotating support so that the rotational speed presents a substantially square wave form.

4. The apparatus of claim 2, wherein the control means controls the rotation of the rotating support so that the rotational speed presents a substantially sinusoidal form.

5. The apparatus of claim 1, wherein the rollers are arranged equidistantly from the rotational axis, and rotatingly travel about the rotational axis.

6. The apparatus of claim 1, wherein the control means controls the rotation of the rotating support in conformity with variations in vacuum pressure or quantity of aspiration flow.

7. The apparatus of claim 6, wherein the control means controls the rotation of the rotating support so that, if the vacuum pressure or the quantity of the aspiration flow is varied to be smaller, the rotational speed is larger, and if the vacuum pressure or the quantity of the aspiration flow is varied to be larger, the rotational speed is smaller.

8. The apparatus of claim 7, wherein the control means controls the rotation of the rotating support so that, if the vacuum pressure or the quantity of the aspiration flow is minimal, the rotational speed is the largest, and if the vacuum pressure or the quantity of the aspiration flow is maximum, the rotational speed is the smallest.

9. An irrigation-aspiration apparatus for supplying an irrigation fluid to a subject part under operation and aspirating the supplied irrigation fluid and tissue removed from the subject part, the apparatus comprising:

an aspiration tube through which the supplied irrigation fluid and the removed tissue is aspirated and disposed of;

a peristaltic aspiration pump having a plurality of rollers that rotatingly travel to compress and occlude the aspiration tube to thereby generate a vacuum pressure in the aspiration tube; and control means for driving and controlling the peristaltic aspiration pump to vary a travelling speed of the roller in accordance with a travelling rotation angle of the roller.

10. The apparatus of claim 9, wherein the control means drives and controls the peristaltic aspiration pump so that the travelling speed is increased once and decreased once when one of the rollers travels by a predetermined amount of the travelling rotation angle.

11. The apparatus of claim 10, wherein the predetermined amount of the travelling rotation angle is determined depending on the number of the rollers provided in the peristaltic aspiration pump.

12. The apparatus of claim 10, wherein the control means drives and controls the peristaltic aspiration pump so that the travelling speed presents a substantially square wave form.

13. The apparatus of claim 10, wherein the control means drives and controls the peristaltic aspiration pump so that the travelling speed presents a substantially sinusoidal form.

14. The apparatus of claim 9, wherein the rollers are arranged equidistantly from a rotational axis, and rotatingly travel about the rotational axis.

15. The apparatus of claim 9, wherein the peristaltic aspiration pump has a rotating support provided with the rollers that rotatingly travel about a rotational axis of the rotating support, and the control means controls rotation of the rotating support so that a rotational speed of the rotating support is varied in accordance with the rotation angle of the rotating support.

* * * * *